(12) United States Patent
Mueller

(10) Patent No.: US 9,611,058 B2
(45) Date of Patent: Apr. 4, 2017

(54) FILLING DEVICE AND CONTROLLER FOR FILLING AN ADMINISTRATION CONTAINER

(71) Applicant: Roche Diagnostics Operations, Inc., Indianapolis, IN (US)

(72) Inventor: Marcel Mueller, Frenkendorf (CH)

(73) Assignee: Roche Diabetes Care, Inc., Indianapolis, IN (US)

(*) Notice: Subject to any disclaimer, the term of this patent is extended or adjusted under 35 U.S.C. 154(b) by 378 days.

(21) Appl. No.: 14/482,030

(22) Filed: Sep. 10, 2014

(65) Prior Publication Data
US 2014/0373968 A1    Dec. 25, 2014

Related U.S. Application Data

(63) Continuation of application No. PCT/EP2012/054388, filed on Mar. 13, 2012.

(51) Int. Cl.
| | |
|---|---|
| *B65B 1/04* | (2006.01) |
| *B65B 3/00* | (2006.01) |
| *A61J 1/22* | (2006.01) |
| *A61J 1/20* | (2006.01) |

(52) U.S. Cl.
CPC ............ *B65B 3/003* (2013.01); *A61J 1/2089* (2013.01); *A61J 1/22* (2013.01); *A61J 2200/70* (2013.01); *A61J 2200/76* (2013.01); *A61M 2209/045* (2013.01)

(58) Field of Classification Search
CPC ...... B65B 3/003; A61J 1/2089; A61J 2200/76
See application file for complete search history.

(56) References Cited

U.S. PATENT DOCUMENTS

| | | | |
|---|---|---|---|
| 2004/0044332 A1 | 3/2004 | Stergiopulos | |
| 2009/0082757 A1 | 3/2009 | Rogers | |
| 2011/0257591 A1 | 10/2011 | Nelson et al. | |
| 2012/0197184 A1* | 8/2012 | Okuda | A61J 1/2096 604/65 |

FOREIGN PATENT DOCUMENTS

| | | |
|---|---|---|
| EP | 2332600 A1 | 6/2011 |
| WO | 9847552 | 10/1998 |
| WO | 2005002652 A2 | 1/2005 |
| WO | 2006048114 A1 | 5/2006 |
| WO | 2008025385 A1 | 3/2008 |
| WO | 2008063429 A3 | 5/2008 |

* cited by examiner

*Primary Examiner* — Jason K Niesz
(74) *Attorney, Agent, or Firm* — Roche Diabetes Care, Inc.

(57) ABSTRACT

A filling device is described which is configured to control the process of filling a medical or therapeutic fluid from a supply container containing the medical or therapeutic fluid into an administration container that is in fluid connection with the supply container. The filling device includes a volume control system configured to control the volume of the administration container and a pressure detection system configured to detect a pressure value related to the pressure inside the supply container. The filling device is further configured to perform the process steps of filling the administration container by: directing the volume control system to decrease the volume of the administration container, directing the pressure detection system to detect a pressure value, and directing the volume control system to increase the volume of the administration container if an increase criterion depending on the pressure value is fulfilled.

14 Claims, 6 Drawing Sheets

FILLING DEVICE AND CONTROLLER FOR FILLING AN ADMINISTRATION CONTAINER

CROSS-REFERENCE TO RELATED APPLICATIONS

The present application is a continuation of International Application No. PCT/EP2012/054388, filed on Mar. 12, 2012, which is hereby incorporated in its entirety.

TECHNICAL FIELD

The present disclosure relates to a filling device, a filling controller and a method of filling a medical or therapeutic fluid from a supply container containing the medical or therapeutic fluid into an administration container being in fluid connection with the supply container.

BACKGROUND

Devices for delivering a medical or therapeutic fluid, such as, for example, insulin pumps, are widely used. In a number of applications, in particular in the self-therapy of diabetes mellitus via continuous subcutaneous insulin infusion (CSII), the devices are used and operated directly by a patient, e.g. by a person with diabetes.

Most of these devices include or are designed to receive an administration container for the medical or therapeutic fluid. Typically, the administration device is realized as a cartridge having a cartridge body with a longitudinal axis and a piston that is movable along the longitudinal axis inside the cartridge body. In order to apply the medical or therapeutic fluid, the piston is coupled to a drive configured to displace the piston in a controlled way, such that fluid in the administration is forced into a catheter or infusion line. This type of device is known as "syringe driver". Initially, the administration container is empty and needs to be filled by the patient prior to use.

Patients using devices for delivering a medical or therapeutic fluid often have preferred medical or therapeutic fluids, which are available in supply containers of different forms. Insulin, which is a medical or therapeutic fluid, is available, for example, in so called vials, which are supply containers typically made from glass and having an access to the insulin on one side through a septum, a membrane that can be perforated or punctured by a cannula, typically a syringe cannula. Insulin is also distributed in so called pen-cartridges, which generally are cylindrical supply containers having on one side also a septum for accessing the insulin, and having on the other side a movable piston. Pen-cartridges are designed for use in dedicated injection devices, so-called pen-type injectors.

For use in delivery devices such as in insulin pumps, the medical or therapeutic fluid has to be filled from the supply container into the administration container, as explained above. In dependence of the design of the administration container and the type of supply container, a variety of filling procedures exist. However, filling procedures are particularly disliked by many patients, as they are known to be cumbersome and to involve a number of delicate handling steps. The filling procedure is especially critical for persons with additional handicaps such as tactile or visual disabilities, which often result as a long-term side effect of diabetes. Depending on the filling volume, the type of the medical or therapeutic fluid, and/or the user's individual needs, it is required to fill an administration container every few days, in particular in diabetes therapy.

Manually filling an administration container with a medical or therapeutic fluid from a vial requires temporarily attaching a syringe-handle to a movable piston of the administration container, thus temporarily modifying the administration container into a syringe. With the syringe obtained, an air pressure is generated inside the vial. In a second step, the air pressure presses the medical or therapeutic fluid from the vial into the syringe. Filling from a pen-cartridge is provided by applying a pushing pressure on the moveable piston of the pen-cartridge, such that the medical or therapeutic fluid is depleted from the pen-cartridge into the administration container. In filling procedures, particular attention is given to avoid formation of air bubbles that are likely to occur during the procedure and need to be removed prior to use of the filled administration container.

WO 2006/048114 discloses a filling process for filling a container with an injection or infusion fluid. A suction device is actuated by a motor to suck the injection or infusion fluid into the container. A vibration unit may be actuated to remove air bubbles from the liquid after filling the container. Filling may be performed by an insulin pump comprising an insulin container and configured to deliver insulin to a patient. The supply container, for example a flexible container, must be designed such, that suction of the medical or therapeutic fluid from the supply container is enabled.

EP 2 332 600 discloses filling a container with a liquid drug from a drug reservoir. The container is connected to the drug reservoir. The inside volume of the container is reduced, thereby displacing a gaseous medium, typically air, from the container into the drug reservoir. In a next step, the inside volume of the container is increased, thereby displacing liquid drug from the drug reservoir into the container. The steps of reducing and increasing the inside volume of the container are performed successively more than once, thus realizing a multi-step filling procedure of the container. By multi-step filling, the operational pressure, and, accordingly, the pressure gradient, is reduced as compared to a single-step filling procedure, thus avoiding the generation of air or gas bubbles. The filling procedure as disclosed in EP 2 332 600, however, is not suited for pen-cartridges as drug container, since the movable piston of the pen-cartridge may be pushed out of pen-cartridge when displacing gaseous medium from the container into the pen-cartridge.

BRIEF SUMMARY

Embodiments of the present disclosure may comprise one or more of the features recited in the claims, and/or one or more of the following features and combinations thereof.

In an embodiment of a filling device of the present disclosure, the filling device is configured to control the process of transferring a medical or therapeutic fluid from a supply container containing the medical or therapeutic fluid into an administration container being in fluid connection with the supply container. The exemplary filling device comprises a volume control system configured to control the volume of the administration container, and a pressure detection system configured to detect a pressure value related to the pressure inside the supply container. The filling device is also configured to perform the process steps of filling the administration container by directing the volume control system to decrease the volume of the administration container, directing the pressure detection system to detect a pressure value, and directing the volume control system to increase the volume of the administration container if an increase criterion depending on the pressure value is fulfilled.

In at least one embodiment of the filling device, the device may be further configured to repeat the process steps of filling the administration container, in particular a fixed number of times and/or until a fill level of the administration container reaches a threshold, wherein the fill level is detected using a fill level detection system. The filling device may optionally be further configured so that the increase criterion is fulfilled if the pressure value reaches or exceeds a threshold.

In at least one embodiment of the filling device, the device may further comprise a pressure data store configured to store data related to pressure values detected by the pressure detection system, wherein the filling device is further configured so that the increase criterion depends on data stored in the data store. The increase criterion may optionally be fulfilled in some embodiments if the current pressure value assumes or exceeds an extremum. Additionally, the increase criterion may optionally be fulfilled if the current pressure value either reaches or exceeds a threshold or if the current pressure value assumes or exceeds an extremum, in particular a maximum.

In at least one embodiment of the present disclosure, a filling controller is described. The exemplary filling controller is configured to control the filling process performed by an embodiment of the filling device of the present disclosure. The filling controller comprises a volume control module configured to direct the volume control system to increase or decrease a volume of the administration container, a pressure detection module configured to detect a pressure value related to the pressure inside the supply container by using the pressure detection system, and a filling module configured to perform the process steps of filling the administration container. Such steps for filling include directing the volume control module to decrease the volume of the administration container, directing the pressure detection module to detect a pressure value, and directing the volume control module to increase the volume of the administration container if an increase criterion depending on the pressure value is fulfilled.

In at least one embodiment of the filling controller, the filling module is further configured to repeat the process steps of filling the administration container, by a fixed number of times and/or until a fill level of the administration container reaches a threshold, wherein the filling controller includes a fill level detection module configured to detect a fill level of the administration container using a fill level detection system.

In at least one embodiment of the present disclosure, the filling controller further comprises a pressure data store configured to store data related to pressure values detected by a pressure detection system, wherein the filling module is configured that the increase criterion depends on data stored in the data store. The filling module may optionally be configured so that the increase criterion is fulfilled if the pressure value reaches or exceeds a threshold or an extremum.

In at least one embodiment of the present disclosure, an administration device for delivering a medical or therapeutic fluid, such as an insulin pump, is described. The administration device comprises or is designed to receive an embodiment of an administration container for storing the medical or therapeutic fluid. The administration device further comprises an embodiment of a filling device according to the present disclosure and in particular a filling controller.

In at least one embodiment of the present disclosure, a method of filling a medical or therapeutic fluid from a supply container containing the medical or therapeutic fluid into an administration container being in fluid connection with the supply container is described. The method comprising the steps of decreasing the volume of the administration container, detecting a pressure value related to a pressure inside the supply container, and increasing the volume of the administration container if an increase criterion depending on the pressure value is fulfilled.

In an embodiment of the method of the present disclosure, the steps of filling the administration container are repeated, in particular a fixed number of times and/or until a fill level of the administration container reaches a threshold. Optionally, the increase criterion may be fulfilled if the pressure value reaches or exceeds a threshold or an extremum.

In at least one embodiment of the present disclosure, a computer program product is disclosed. The computer program product comprises a computer readable medium having stored thereon computer program code configured to be executed on one or more processors of a filling device, of a filling controller, or of an administration device, such that the following steps of filling an administration container are performed: decreasing the volume of the administration container, detecting a pressure value related to a pressure inside the supply container, and increasing the volume of the administration container if an increase criterion depending on the pressure value is fulfilled.

BRIEF DESCRIPTION OF THE DRAWINGS

In order to facilitate a fuller understanding of the present disclosure, reference is now made to the appended drawings. These references should not be construed as limiting the present disclosure, but are intended to be exemplary only.

DETAILED DESCRIPTION

Figure 1:
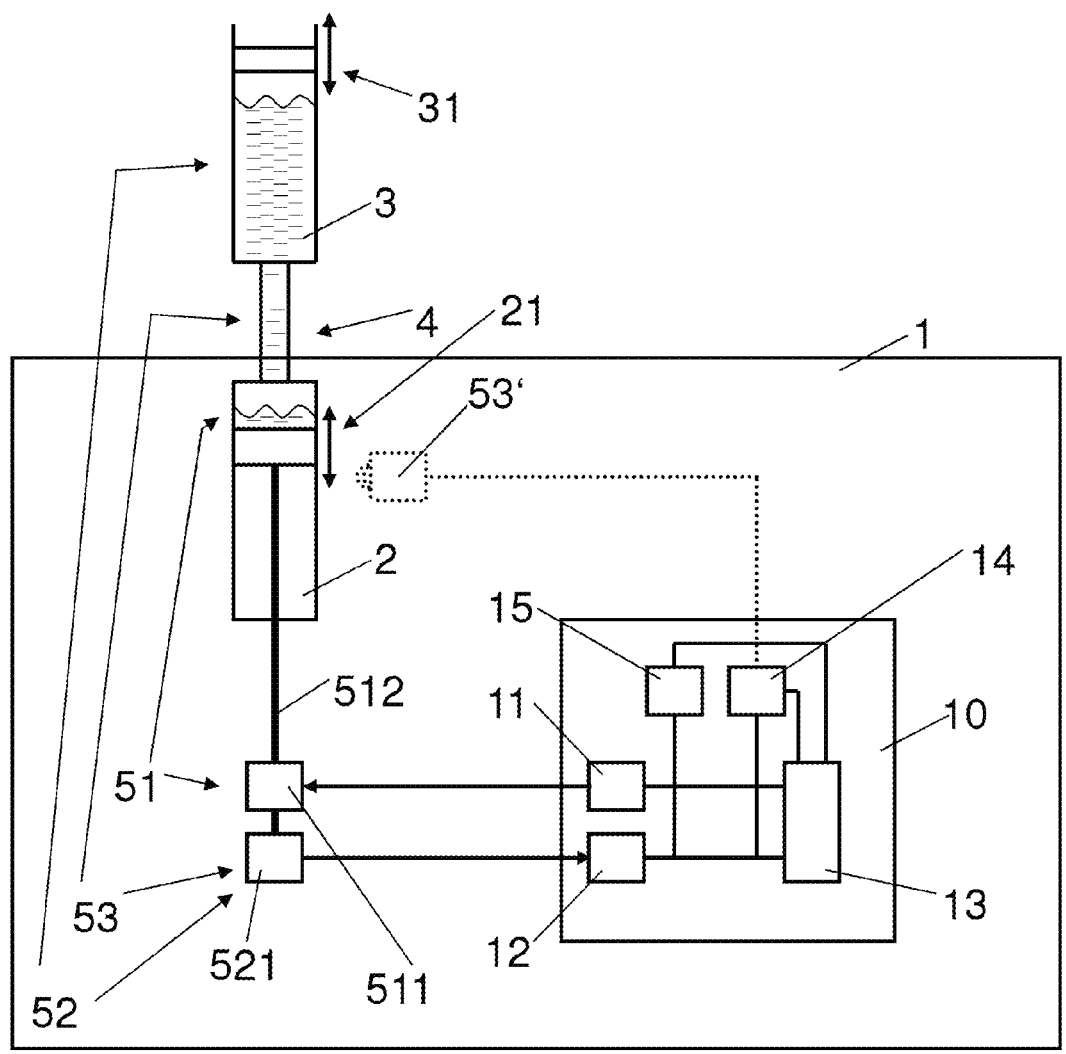
FIG. 1 is a schematic representation of a filling device for filling an administration container connected in fluid connection with a supply container, according to at least one embodiment of the present disclosure.

It is an object of at least one embodiment of the present disclosure to provide a filling device, a filling controller and a method of filling a medical or therapeutic fluid from a supply container containing the medical or therapeutic fluid into an administration container being in fluid connection with the supply container. In particular, it is an object of the present disclosure to provide a filling device, a filling controller and a method of filling a medical or therapeutic fluid from a supply container containing the medical or therapeutic fluid into an administration container being in fluid connection with the supply container, which filling device, filling controller and method provide for a more comfortable procedure of filling an administration container from a supply container. In particular use of different types of supply containers is enabled, e.g. vials or pen-cartridges, such that in case of a pen-cartridge, the risk of pushing a piston out of the pen-cartridge is minimized. Moreover generating air bubbles is avoided or at least reduced, largely independent of the supply container. According to the present disclosure, these objects are achieved through the features of the independent claims. In addition, further advantageous embodiments follow from the dependent claims and the description.

The above-mentioned objects may be achieved in that a filling device, which is configured to control the process of filling a medical or therapeutic fluid from a supply container containing the medical or therapeutic fluid into an administration container being in fluid connection with the supply container, includes a volume control system configured to control the volume of the administration container and a pressure detection system configured to detect a pressure value related to the pressure inside the supply container. The filling device is further configured to perform the process steps of filling the administration container by: directing the volume control system to decrease the volume of the administration container, directing the pressure detection system to detect a pressure value, and directing the volume control system to increase the volume of the administration container if an increase criterion depending on the pressure value is fulfilled.

Decreasing the volume of the exemplary administration container presses air and/or medical or therapeutic fluid that is already present in the administration container into the exemplary supply container, such that in a later step the volume of the administration container can be increased again, thus filling the administration container with the medical or therapeutic fluid from the supply container. During the process of filling the administration container, the supply container may be arranged above the administration container. For example, the increase criterion is computed according to any function depending on the pressure value. The pressure value reflects the current pressure in the supply container and if the increase criterion is fulfilled, the volume of the administration container is increased again, such that the pressure inside the supply container that was built-up when decreasing the volume of the administration container, is decreased again, thereby pressing medical or therapeutic fluid into the administration container.

Thus, filling of the administration container is based on first generating a relative over pressure in the supply container by decreasing the volume of the administration container. Subsequently, when increasing the volume of the administration container again, this over pressure in the supply container is used for pressing medical therapeutic fluid from the supply container into the administration container. If a pen cartridge is used as a supply container, detecting the pressure via the pressure detection system allows for keeping a movement of the piston of the pen cartridge limited such that pushing the piston out of the cartridge is avoided. As will be discussed below in more detail, a suited increase criterion may include a threshold or an extremum, in particular a maximum of the pressure-vs-time curve, or a combination of both, such that the over pressure in the supply container does not reach a level where the piston is pushed out of the supply container. Moreover, generation of bubbles is substantially prevented. In this way, the pressure gradient between the two containers is further limited to a level where insulin flows laminar from one container to the other and air bubbles are avoided.

The pressure detection system may be designed to measure a fluidic pressure directly, for example using a fluidic pressure sensor. Alternatively, the fluidic pressure may be measured indirectly, in particular through a force sensor configured to be used as pressure detection system that detects or measures a force that is applied onto a piston of the administration container. Due to the fluidic coupling of the administration container and the supply container, this force also reflects the pressure inside the supply container.

In an embodiment, the filling device may be further configured to repeat the process steps of filling the administration container, in particular a fixed number of times and/or until a fill level of the administration container reaches a threshold, wherein the fill level is detected using a fill level detection system. Hence, the process steps of filling the administration container are repeated as described above. In this way, a multi-step filling of the administration container is realized, where only a portion of the volume is transferred from the supply container to the administration container in each step. In such a procedure, the required pressure gradient that drives the fluid transfer is realized, thus avoiding or at least reducing the generation of air bubbles in the medical or therapeutic fluid. In some of those embodiments, a counter may be provided that counts the number of repetitions. The filling process may be finally stopped at a pre-programmed number of repetition cycles, such as 5, 10, or 20 repetition cycles in order to ensure complete filling of the administration container. In such an embodiment, the number of repletion cycles is generally uncritical and may therefore include some safety margin. Once the administration container is fully filled, further repletion cycles will only shift medical or therapeutic fluid backwards and forwards between the supply container and the administration container without any harmful effect. Alternatively, or additionally, a fill level of the administration container is monitored and the steps are repeated until the fill level of the administration container reaches a threshold. In this case, the filling controller includes a fill level detection system which is configured to detect a fill level of the administration container. In the steps of increasing the volume of the administration container following a previous decrease, the administration container is increased to its maximum value in each repletion cycle.

In at least one embodiment, the filling device is configured such that the increase criterion is fulfilled if the pressure value reaches or exceeds a threshold. Accordingly, the pressure in the supply container is kept below a threshold all times. The threshold may be selected such that the pressure gradient in the fluid is limited not to exceed values where turbulent flow may occur, thus preventing the generation of air bubbles. A pressure threshold is a particularly suited increase criterion if a vial is used as supply container. For such a configuration, decreasing the volume of the administration container is associated with a steady pressure increase, since the volume of the vial is substantially constant.

In at least one embodiment, the filling device further comprises a pressure data store configured to store data related to pressure values detected by the pressure detection system, wherein the filling module is configured such that the increase criterion depends on data stored in the data store. For example, a time series of pressure values is stored in the data store, wherein any function such as moving average, derivation or any other function is applied to the stored pressure values in order to determine, if the increase criterion is fulfilled.

In at least one embodiment, the filling device is further configured such that the increase criterion is fulfilled if the current pressure value assumes or exceeds an extremum, in particular a maximum. In an embodiment including a pressure data store as discussed above, an extremum of the pressure is determined by comparing a current value with one or multiple past values stored in the pressure data store.

A pressure extremum is an exemplary increase criterion where a pen cartridge is used as a supply reservoir. When the volume of the administration container is decreased and the pressure inside the pen cartridge as supply container increased, a corresponding force acting on the movable piston of the supply container (referred to as supply piston) increases as well. Depending on frictional forces between the supply piston and the supply container, the supply piston starts moving if the pressure inside the supply container exceeds a threshold. In case the volume of the administration container is further decreased and the pressure inside the supply container is accordingly further increased, the supply piston may be pushed out of the supply container, whereby the medical or therapeutic fluid may be spilled or polluted. This may be avoided by switching from decreasing the volume of the administration container to increasing its volume, thus allowing fluid to be pressed from the supply container into the administration container via the over pressure in the supply container.

In at least one embodiment, the filling device is further configured so that the increase criterion is fulfilled if the current pressure value either reaches or exceeds a threshold or if the current pressure value assumes or exceeds an extremum, in particular a maximum. In such an embodiment, the filling device stops decreasing the volume of the administration container and starts increasing its volume if the pressure either reaches or exceeds the threshold or the extremum, whatever happens first. Such an embodiment of the filling controller allows filling the administration container from a vial. The threshold may be selected somewhat above the pressure at which the maximum for a pen cartridge as supply reservoir may occur. This design ensures that both types of cartridges may be used and ensures that the supply piston is not pushed out of the supply container.

In addition to a filling device, at least one embodiment of the present disclosure is directed to a filling controller configured to control the filling process performed by a filling device. The filling controller comprises: a volume control module configured to direct the volume control system to increase or decrease a volume of the administration container, a pressure detection module configured to detect a pressure value related to the pressure inside the supply container by using the pressure detection system, and a filling module configured to perform the process steps of filling the administration container by: directing the volume control module to decrease the volume of the administration container, directing the pressure detection module to detect a pressure value, and directing the volume control module to increase the volume of the administration container if an increase criterion depending on the pressure value is fulfilled. In a variant, the filling module is further configured to repeat the process steps of filling the administration container, in particular a fixed number of times and/or until a fill level of the administration container reaches a threshold, wherein the filling controller includes a fill level detection module configured to detect a fill level of the administration container using a fill level detection system. In a variant, the filling controller further comprises a pressure data store configured to store data related to pressure values detected by a pressure detection system, wherein the filling module is configured that the increase criterion depends on data stored in the data store. In a variant, the filling module is further configured that the increase criterion is fulfilled if the pressure value reaches or exceeds a threshold or an extremum, in particular a maximum.

In addition to a filling device and a filling controller, the present disclosure is directed towards an administration device for delivering a medical or therapeutic fluid, in particular an insulin pump, comprising or being designed to receive an administration container for storing the medical or therapeutic fluid, the administration device further comprising a filling device according to the present disclosure and in particular a filling controller according to the present disclosure.

In such an embodiment, the volume control system may be identical with the drive system that is used for the medicine administration performed by the administration device. The pressure detection system may be realized by a force sensor that measures a force applied on the movable piston of the administration container. Such a force sensor is typically present in the administration device for generally monitoring the administration and detecting hazardous operational conditions, such as a blockage or occlusion of the infusion tubing or infusion cannula.

In this way, an administration device as generally known in the art may be modified to include an embodiment of the functionality described in the present disclosure, in particular a filling controller, with the only modifications being in the embedded control code, with no or minimal modifications to the device hardware. An administration device that may be modified in this way is, for example, commercially available by Roche Diagnostics as ACCU-CHEK® Spirit or ACCU-CHEK® Spirit Combo. Typical users of such a system are, for example persons with diabetes.

However, a filling device may also be provided as a separate stand-alone device. It may be used, for example, by a person with diabetes in addition to an insulin pump or by pharmacies offering the filling of administration container as service.

In addition to the filling device, the filling controller and the administration device, the present disclosure further relates to a method of filling a medical or therapeutic fluid from a supply container containing the medical or therapeutic fluid into an administration container being in fluid connection with the supply container, the method comprising the steps of: decreasing the volume of the administration container, detecting a pressure value related to a pressure inside the supply container, and increasing the volume of the administration container if an increase criterion depending on the pressure value is fulfilled. In a variant, the steps of filling the administration container are repeated, such as by a fixed number of times and/or until a fill level of the administration container reaches a threshold. In a variant the increase criterion is fulfilled if the pressure value reaches or exceeds a threshold or an extremum.

In addition to the filling device, the filling controller, the administration device, and the method of filling an administration container, the present disclosure further relates to a computer program product comprising a computer readable medium having stored thereon computer program code configured to be executed on one or more processors of a filling device, of a filling controller, or of an administration device, such that the following steps of filling an administration container are performed: decreasing the volume of the administration container, detecting a pressure value related to a pressure inside the supply container, and increasing the volume of the administration container if an increase criterion depending on the pressure value is fulfilled.

FIG. 1 shows schematically an administration container 2, which is connected in fluid connection 4 to a supply container 3. For example, the administration container 2 is included in or received by an insulin pump configured to deliver insulin to a patient according to a specific delivery plan, wherein the administration container 2 is to be filled with a medical or therapeutic fluid, such as insulin, prior to use. Hence, in a variant, the supply container 3 contains insulin which is to be filled into the administration container 2. In an embodiment, the supply container 3 is a vial. In another embodiment, the supply container 3 is a pen-cartridge. In yet another embodiment, the supply container 3 is any suitable container for storing a medical or therapeutic fluid, such as insulin. As schematically shown in FIG. 1, the administration container 2 is configured such that a volume of the administration container 2 is increasable or decreasable, for example through an administration piston 21 which is movably arranged inside the administration container 2, wherein the administration piston 21 is in particular movable along a longitudinal axis of the administration container 2.

A vial is a vessel or bottle to store a medical or therapeutic fluid, wherein access to the fluid is provided, for example, by penetrating a septum arranged on an opening of the vial. The vial is otherwise closed and does not have further openings. In contrast to a vial, a pen-cartridge is a tubelike container to store the medical or therapeutic fluid. The tubelike pen-cartridge has openings on both of its ends, wherein access to the medical or therapeutic fluid is provided, for example, by penetrating a septum arranged on one end of the pen-cartridge. The other end of the pen-cartridge is closed, for example with a movable cartridge piston. In a variant of use of the pen-cartridge, the cartridge piston is moved towards the septum, such that the medical or therapeutic fluid is delivered out of the pen-cartridge.

In an embodiment, the fluid connection 4 between the supply container 3 and the administration container 2 is established through a transfer cannula, which is temporarily but safely attached to the administration container 2 through a connector device, wherein the transfer cannula is penetrating the septum of the supply container 3, for example the septum of a vial or pen-cartridge. Accordingly, a releasable but reliable fluid connection 4 between the supply container 3 and the administration device 2 is easily established for filling of the administration container 2 with a medical or therapeutic fluid.

Different types of supply containers 3 are available, such as, vials or pen-cartridges, each type of supply container 3 requiring a dedicated filling procedure. A particular type of a supply container 3 is selected if filling of the administration container 2 is required. For example, vials and pen-cartridges are available containing different types of medical or therapeutic fluid, for example different types of insulin. Or in certain geographic regions, such as in different countries, only certain types of supply containers 3 are available, such as only vials or only pen-cartridges. In FIG. 1, a supply container 3 is schematically shown having the properties of a pen-cartridge, namely having a septum on the end facing the fluid connection 4 and having a movable supply piston 31 on the other end. However, in other embodiments other types of supply container 3 are used when filling of the administration container 2 is required. As shown schematically in FIG. 1, the administration container 2 is arranged in or received by a filling device 1. As discussed above, the filling device 1 may be designed such that different types of supply containers 3 may be used.

In a variant, filling the administration container 2 with a medical or therapeutic fluid contained in the supply container 3 is performed by first decreasing a volume of the administration container 2. In an embodiment, the volume of the administration container 2 facing the fluid connection 4 is decreased by moving the administration piston 21 towards the fluid connection 4. For example, the administration piston 21 is moved using a volume control system 51. In an embodiment, the volume control system 51 includes a drive rod 512, wherein one end of the drive rod 512 is attached to the administration piston 21 via a releasable push-pull connection, such as a bayonet connector or screw-like connector, thus allowing a controlled movement of the administration piston 21 towards and away from fluid connection 4. Further variants of reusable couplings that may be used are disclosed, e.g. in WO 2005/002652, WO 2008/025385, or WO 2008/063429.

The other end of the drive rod 512 is actuated through a drive 511. In a variant, the drive 511 includes an electrical motor, such as a standard DC motor, a brushless DC motor or a stepper motor, and a gear mechanism, such that by actuating the electrical motor, for example through a drive control signal, the drive rod 512 is actuated by the drive 511 such that the administration piston 21 is moved towards the fluid connection 4 or away from the fluid connection 4. For example, increasing or decreasing a volume of the administration container 2 is selected by selecting a specific drive control signal. As discussed above, the filling device 1 may be integrated into an administration device, such as an insulin pump. For those embodiments, the drive 511 and the drive rod 512 are integral with the drive unit of the administration device. Generally suited designs of insulin pumps that may be used are disclosed, e.g. in WO 98/47552 or WO 2008/063429. Those and similar designs may also be used in embodiments of the filling device 1 which are designed as stand-alone devices.

In a further embodiment, a volume of the administration container 2 is decreased or increased through collapsing or expanding a flexible container, or in any other manner.

When decreasing a volume of the administration container 2 connected to the fluid connection 4, gas or fluid is pressed through the fluid connection 4 into the supply container 3, for example air or medical or therapeutic fluid already filled into the administration container 2 in previous repletion cycles. Here and in the following, it is generally assumed that the administration container is filled with gas, in particular air, up to its maximum filling volume at the beginning of the filling process. Accordingly, the pressure inside the supply container 3 increases. In a variant, air is pressed into the supply container 3 when decreasing the volume of the administration container 2 connected to the fluid connection 4 and medical or therapeutic fluid contained in the supply container 3 is filled into the administration container 2 when increasing the volume of the administration container 2 connected to the fluid connection 4. In an embodiment, through repetition of decreasing and increasing the volume of the administration container 2 connected to the fluid connection 4, the medical or therapeutic fluid contained in the supply container 3 is filled stepwise into the administration container 2 in a number of repetition cycles. Starting from the administration container being fully filled with air at the beginning, the amount of air is decreased and the amount of medical or therapeutic fluid is increased in each repletion cycle.

When pressure inside the supply container 3 increases, a corresponding force acting on the supply piston 31 increases as well. For example depending on frictional forces between the supply piston 31 and the supply container 3, the supply piston 31 begins to move in the direction away from the fluid connection 4 if the pressure inside the supply container 3 exceeds a threshold. In case of the movement of the supply piston 31 being continued, supply piston 31 may be moved or pushed out of the supply container 3, whereby the medical or therapeutic fluid may be spilled or polluted. Hence, the supply piston 31 must not be moved out of the supply container 3.

In FIG. 1, the reference sign 52 refers to a pressure detection system 52. In an embodiment, the pressure detection system 52 includes a force sensor 521 sensing the force applied by the drive rod 512 to the drive administration piston 21. Through a function depending on the stiffness and/or compressibility of the drive rod 512 and/or of the gas and/or fluid between the delivery container piston 21 and the inside of the supply container 3, the pressure inside the supply container 3 may be determined. In a variant, the force sensor 521 is arranged between the drive 511 and the enclosure of the administration device, for example between the motor and the casing of an insulin pump. In a variant, the force sensor 521 includes a force sensing arrangement that determines the force that is exerted onto container piston 21 via drive rod 512. Such a force sensor may, for example be realized by a force sensitive resistor, or a strain gauge beam arrangement. In other embodiments, the pressure detection system 52 includes a torque transducer that determines the torque that is exerted by the drive 511 onto the drive rod 512. In another variant, the force sensor 521 includes a voltage and/or current sensor for sensing electrical power delivered to drive 511, or any other sensor configured to sense a force applied by the drive 511. Generally, the pressure detection system may be designed in the same way as known in the art for administration devices, such as insulin pumps, for detecting hazardous situations, such as fluidic occlusions or blockages. In embodiments of a filling controller that comprise such an administration device, a common arrangement may be used for both purposes. Alternatively, the pressure detection system may be designed to directly measure the fluidic pressure inside the administration container 2, inside the supply container 3 or inside the fluid connection 4.

In FIG. 1, reference sign 10 refers to an exemplary filling controller. The filling controller 10 comprises a volume control module 11, a pressure detection module 12, and a filling module 13. The volume control module 11 is configured to direct the volume control system 51 to increase or decrease a volume of the administration container 2. For example, the volume control module 11 may be configured to generate a drive control signal for controlling the drive 511 to advance or retract the drive rod 512. The pressure detection module 12 may be configured to detect a pressure value related to the pressure inside the supply container 3 by using the pressure detection system 52. For example, the pressure detection module 12 may be configured to receive a force signal generated by force sensor 521, wherein the pressure detection module 12 may be further configured to compute or determine a pressure value related to the pressure inside supply container 3. For example, the pressure value equals the force signal received from force sensor 521. The filling module 13 may be configured to perform the steps of filling the administration container 2 by: directing the volume control module 11 to decrease the volume of the administration container 2, directing the pressure detection module 12 to detect a pressure value, and directing the volume control module 11 to increase the volume of the administration container 2 if an increase criterion depending on the pressure value is fulfilled. For example, the increase criterion is fulfilled if the pressure value assumes or exceeds a threshold or an extremum, in particular a maximum.

The filling controller 10 comprises various functional modules or systems, including the volume control module 11, the pressure detection module 12, and the filling module 13. Depending on the embodiment, these functional modules are implemented by way of programmed software modules, comprising computer code stored on a computer-readable medium, by way of hardware components, or by way of a combination of software and hardware.

In a variant, the filling controller 10 includes a fill level detection module 14 configured to detect a fill level of the administration container 2 using a fill level detection system 53, 53'. For example, the filling controller 10 is configured to stop operation if the fill level exceeds a threshold.

In an embodiment denoted with reference sign 53, the fill level detection system 53 includes the force sensor 521. When filling the administration container 2, during the step of decreasing the volume of the administration container 2, air is pressed from the administration container 2 through the fluid connection 4 into the supply container 3. As soon as the administration container 2 is full, during the step of decreasing the volume of the administration container 2, medical or therapeutic fluid is pressed from the administration container 2 through the fluid connection 4 into the supply container 3. As the force to press medical or therapeutic fluid through the fluid connection 4 is larger than the force needed to press air through the fluid connection 4, a difference of the force applied by the drive 511 to the administration rod 512 can be detected using the force sensor 521. As soon as an increase in the force during decrease of the volume of the administration container 2 is detected, it can be concluded that the administration container 2 is filled to its maximum fill level.

In an embodiment denoted with reference sign 53', the fill level detection system 53' includes a independent technology, such as an optical sensor to detect a refractive index of the administration container 2. The refractive index is detected at a certain location of the administration container 2. When air is contained at this location, the refractive index is different to the case when medical or therapeutic fluid is contained at this location. In a variant, the fill level detection system 53, 53' includes any other technology suitable to detect the fill level of the administration container 2.

In FIG. 1, the reference sign 15 refers to a data store. For example, the data store 15 is configured to receive and store a pressure value related to the pressure inside the supply container 3, which pressure value was detected by the pressure detection module 12. As described above, in an embodiment, the stored pressure value includes a force or in another embodiment, the pressure value includes a pressure. In a variant, the data store 15 is configured to store several pressure values. For example, the steps of filling the administration container 2 are repeated, namely decreasing the volume of the administration container 2, detecting a pressure value related to the pressure inside the supply container 3, and increasing the volume of the administration container 2 if a an increase criterion depending on the pressure value is fulfilled. In a variant, in each repetition the detected pressure value is stored in the data store 15. For example, the data store 15 is configured to store a number N of pressure values, such that in each repetition k a current pressure value pv(k) and for example N−1 past pressure values pv(k−1), pv(k−2), . . . pv(k−(N−1)) are available as a time series in the data store. In a variant, the increase criterion depends of the pressure values stored in the data store. For example, a moving average of the pressure values may be computed and compared to a threshold. In a variant, the increase criterion is fulfilled if the moving average exceeds the threshold. In another example, a derivative of the pressure values may be computed and compared to a threshold. In a variant, the increase criterion is fulfilled if the derivative is negative. In another variant, the increase criterion is fulfilled if the current pressure value pv(k) is smaller than the last pressure value pv(k−1).

In at least one embodiment, the filling controller 10 is built into an administration device such as an insulin pump. For example, the insulin pump may include an administration container 2 for the insulin and a volume control system 51 for controlling the volume of the administration container 2, wherein the volume control system 51 is controlled so that the insulin is delivered in required quantities or amounts to a patient. In a variant, the insulin pump includes a pressure detection system 52, such that critical events during delivery of the insulin are detectable, as for example air bubbles in the delivery system. In a variant, the filling controller 10 makes use of systems and modules already built in into an insulin pump. Accordingly, the filling controller 10 may be easily deployable in a wide variety of devices.

Figure 2:
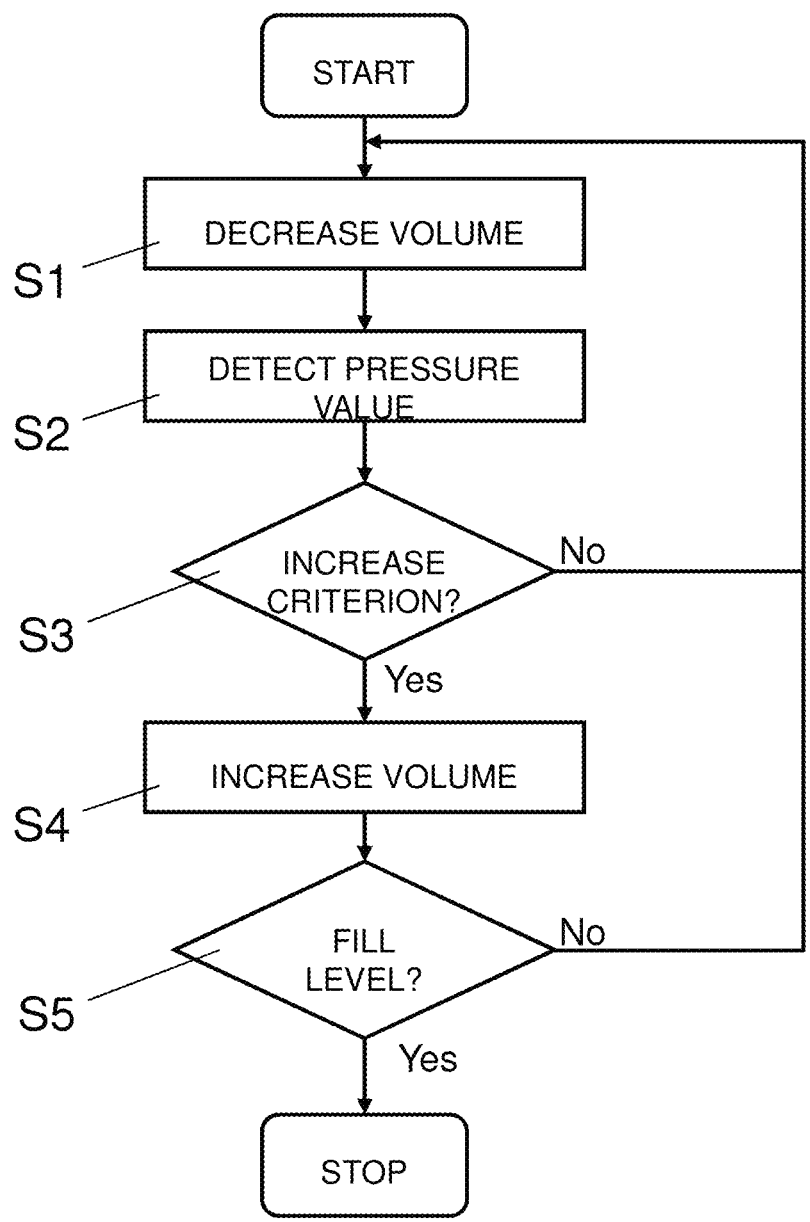
FIG. 2 shows a sequence of steps for filling an administration container being in fluid connection with the supply container, according to at least one embodiment of the present disclosure.

FIG. 2 shows schematically an embodiment of a possible sequence of steps performed for controlling the process of filling a medical or therapeutic fluid from a supply container 3 into an administration container 2 being in fluid connection with the supply container 3. Before the possible sequences of steps are started, the supply container 3 is connected in fluid connection 4 with the administration container 2 and the setup is arranged such that gravity acts from supply container 3 towards administration container 2, i.e. supply container 3 is arranged above administration container 2. At the beginning, administration container 2 may be partly or fully filled with air and typically no medical or therapeutic fluid.

In step S1, the process of filling an administration container 2 with a medical or therapeutic fluid is started by decreasing a volume of the administration container 2, wherein air and/or medical or therapeutic fluid is pressed from the administration container 2 into the supply container 3.

In step S2, a pressure value related to the pressure inside the supply container 3 is detected, for example the force applied to the administration container 2 to decrease the volume of the administration container 2, or any other pressure value related to the pressure inside the supply container 3.

In step S3, it is validated if an increase criterion depending on the pressure value is fulfilled. If the increase criterion is not fulfilled, the procedure of filling the administration container 2 is continued with step S1. If the increase criterion is fulfilled, the volume of the administration container 2 is increased in step S4. Favourably, the volume of the administration container 2 is increased to its maximum filling level.

In step S5, it is validated if a fill level of the administration device 2 has reached a threshold. If the fill level has not reached a threshold, the procedure of filling the administration container 2 is continued with step S1. If the fill level has reached the threshold, the procedure of filling the administration container 2 is stopped.

Figure 3:
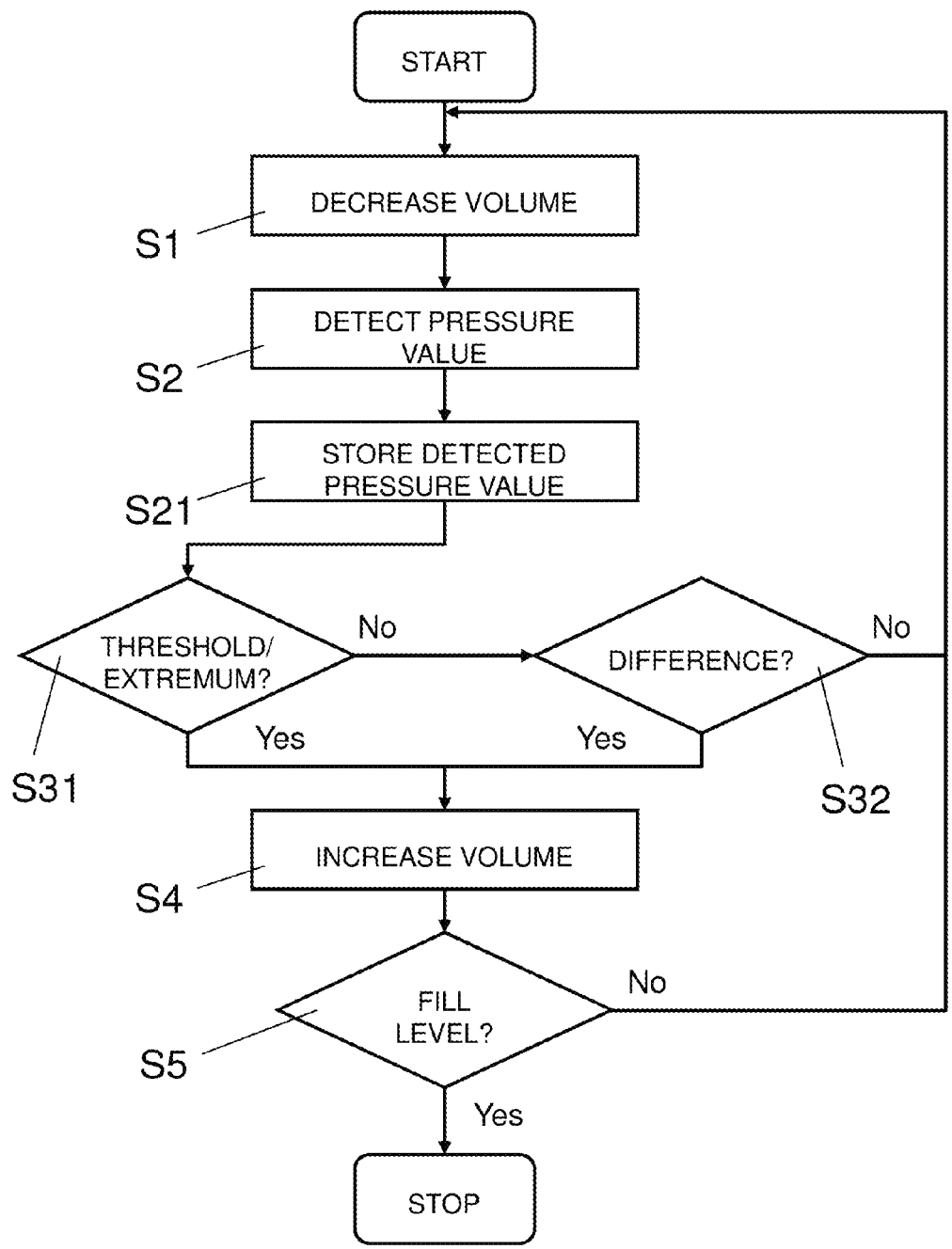
FIG. 3 shows a sequence of steps for filling an administration container being in fluid connection with the supply container, according to at least one embodiment of the present disclosure.

FIG. 3 shows schematically an embodiment of possible sequences of steps performed for controlling the process of filling a medical or therapeutic fluid from a supply container 3 into an administration container 2 being in fluid connection with the supply container 3. Steps S1, S2, S4, and S5 are unchanged with respect to the steps described in connection with FIG. 2.

After step S2, in step S21 the detected pressure value is stored in a data store. Accordingly, during a certain sequence of steps, not only the current pressure value is available, but also the last pressure value detected during the last sequence.

In step S31, the current pressure value is compared to a threshold. If the pressure value exceeds the threshold, the procedure continues with step S4 and the volume of the administration container 2 is increased. Otherwise, the procedure continues with step S32.

In step S32, the difference between the current pressure value and the last pressure value is computed. If the difference is negative, the procedure continues with step S4 and the volume of the administration container 2 is increased. Otherwise, the procedure continues with step S1 and the volume of the administration container is decreased.

In this way, steps, S1, S2, S21, S31, S32, in combination implement a procedure where the volume of administration container 2 is continuously or stepwise decreased until either a pressure threshold is exceeded (Step S31) or a pressure maximum is assumed or passed (negative pressure difference, Step S32). The sequence as shown in FIG. 3 may accordingly be used for filling the administration container 2 out of a pen cartridge or a vial.

Figure 4A:
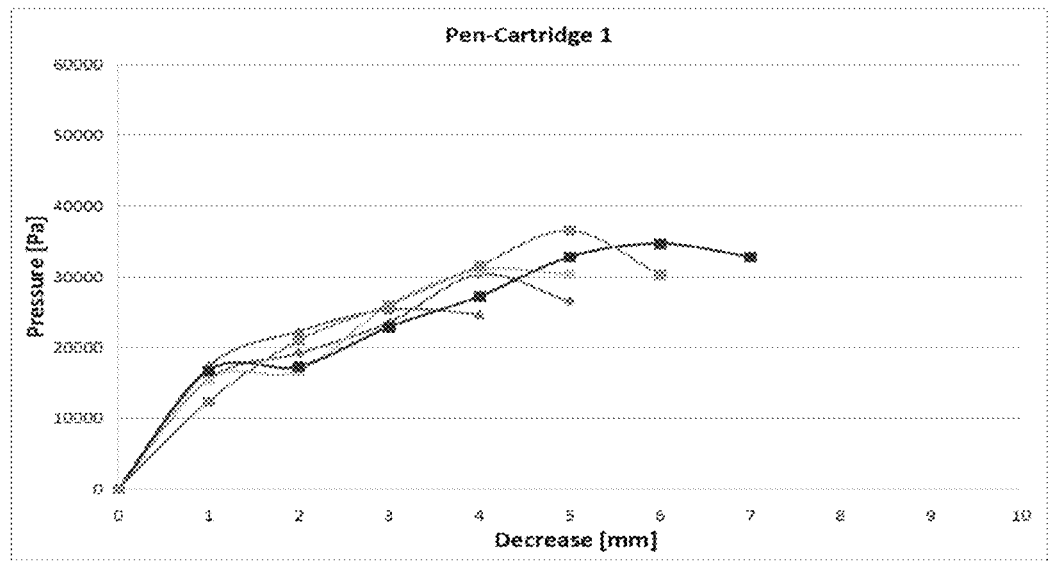
FIGS. 4A, 4B, and 4C show diagrams of the pressure in dependence of the decrease of the volume of the administration container, according to at least one embodiment of the present disclosure.
Figure 4B:
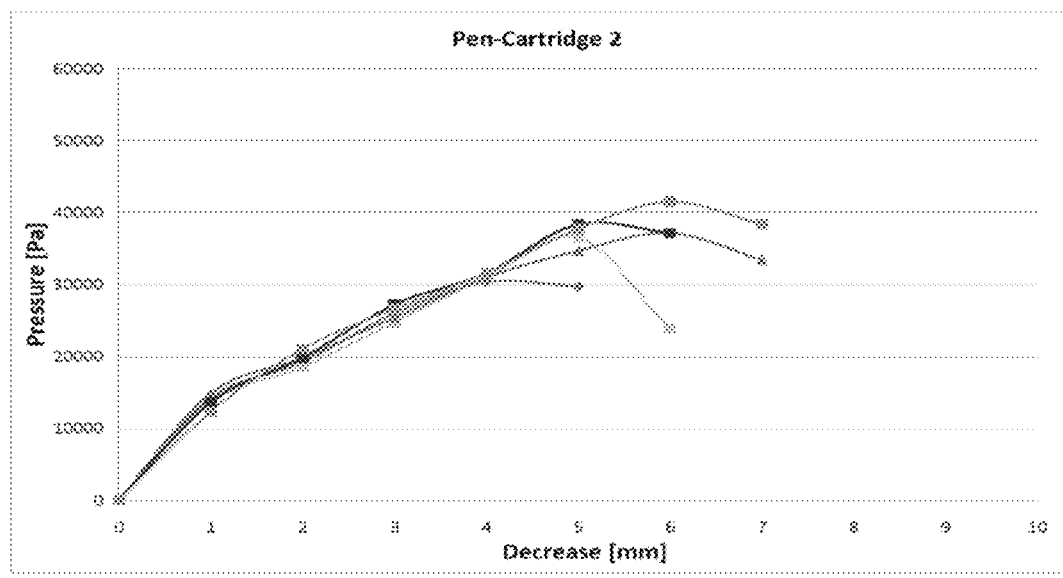
Figure 4C:
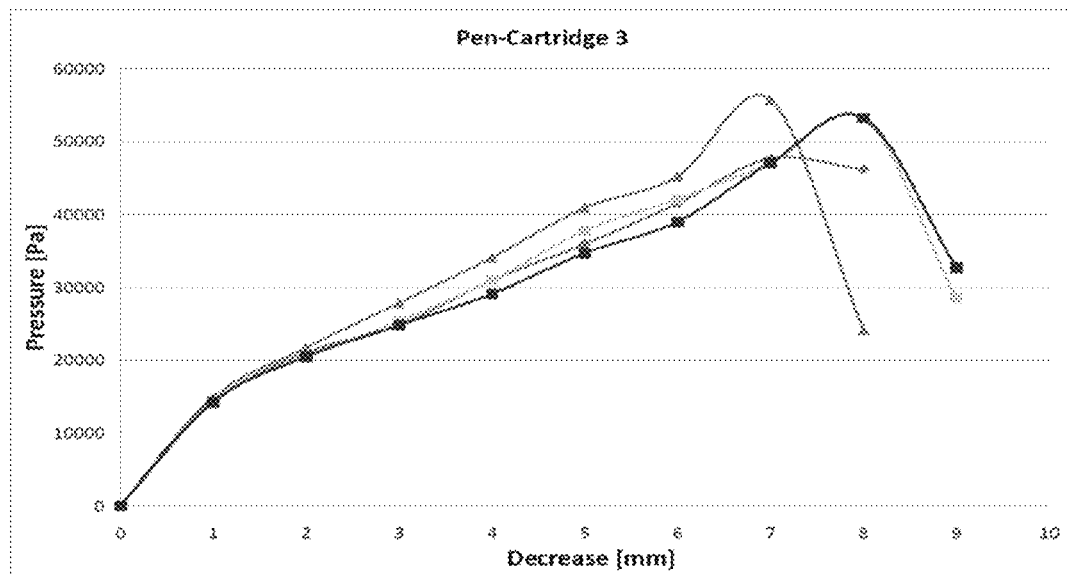

FIGS. 4a, 4b, 4c show the diagrams of the pressure in dependence of the decrease in the volume of the administration container 2. The diagrams are shown for three different types of pen-cartridges. The pressure depends on the displacement in mm of the administration piston 21 of the administration container 2. As can be seen from the diagrams, the pressure decreases when the displacement is around 5.5 mm (FIG. 4a), around 6 mm (FIG. 4b), and around 8 mm (FIG. 4c). In the diagrams, several samples are shown for the same pen-cartridge. The pressure decrease indicates that the supply piston 31 starts to be moved or pushed out of the supply container 3.

An absolute pressure threshold may be chosen somewhat above the maximum values.

Figure 5A:
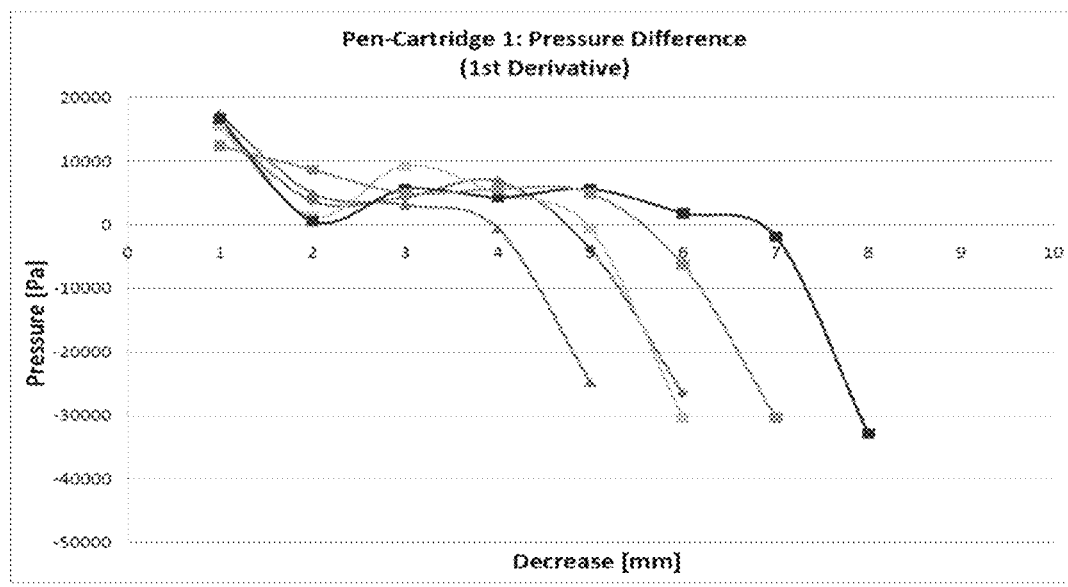
FIGS. 5A, 5B, and 5C show diagrams of the pressure difference in dependence of the decrease of the volume of the administration container, according to at least one embodiment of the present disclosure.
Figure 5B:
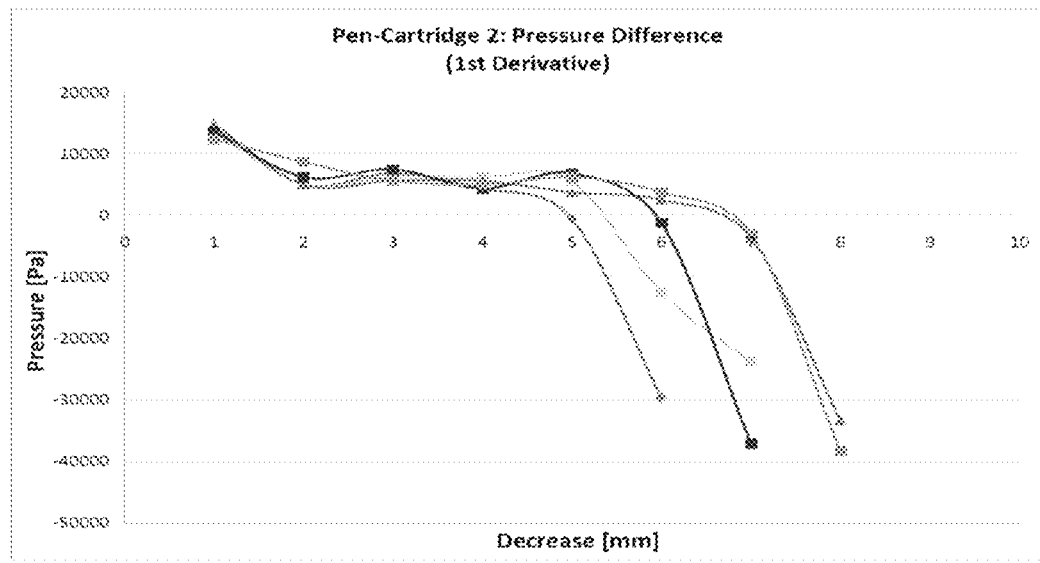
Figure 5C:
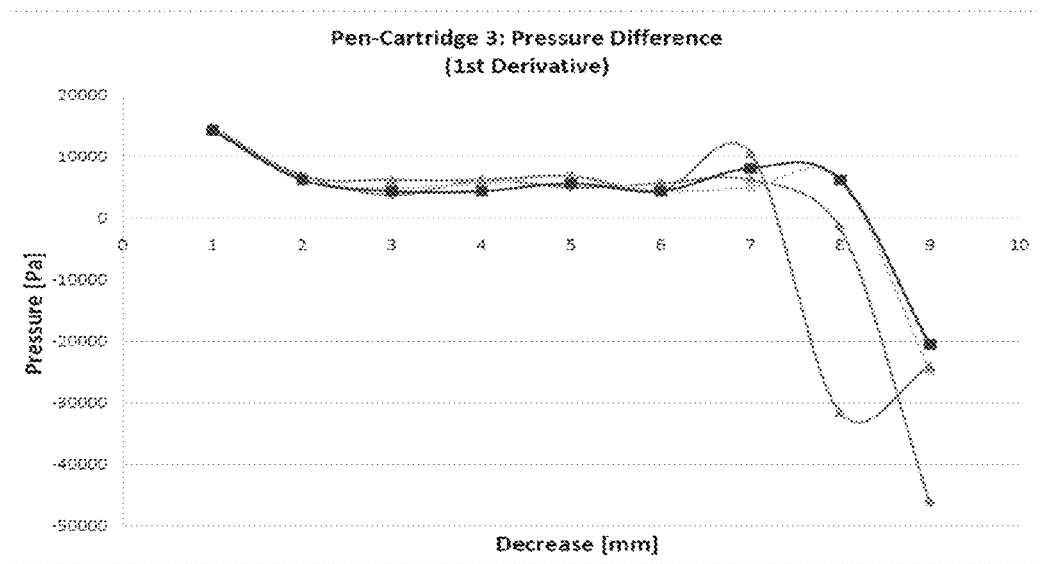

FIGS. 5a, 5b, 5c show the diagrams of the pressure difference in dependence of the decrease in the volume of the administration container 2. The diagrams are shown for three different types of pen-cartridges. The pressure depends on the displacement in mm of the administration piston 21 of the administration container 2. As seen in the diagrams, the pressure difference turns to negative when the displacement is around 5.5 mm (FIG. 5a), around 6 mm (FIG. 5b), and around 8 mm (FIG. 5c). In the diagrams, several samples are shown for the same pen-cartridge.

While various embodiments of filling devices, controllers, and methods for filling an administration container have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

LIST OF REFERENCE NUMERALS 1 filling device
10 filling controller
11 volume control module
12 pressure detection module
13 filling module
14 fill level detection module
15 data store
2 administration container
21 container piston
3 supply container
31 supply piston
4 fluid connection
51 volume control system
511 drive
512 drive rod
52 pressure detection system
521 force sensor
53, 53' fill level detection system

The invention claimed is:

1. A filling device configured to control the process of transferring a medical or therapeutic fluid from a supply container containing the medical or therapeutic fluid into an administration container being in fluid connection with the supply container, the filling device comprising:
a volume control system configured to control the volume of the administration container; and
a pressure detection system configured to detect a pressure value related to the pressure inside the supply container,
wherein the filling device is configured to perform the process steps of filling the administration container by:
directing the volume control system to decrease the volume of the administration container,
directing the pressure detection system to detect a pressure value, and
directing the volume control system to increase the volume of the administration container if an increase criterion depending on the pressure value is fulfilled.

2. The filling device according to claim 1, further configured to repeat the process steps of filling the administration container, in particular a fixed number of times and/or until a fill level of the administration container reaches a threshold, wherein the fill level is detected using a fill level detection system.

3. The filling device according to claim 1, further configured so that the increase criterion is fulfilled if the pressure value reaches or exceeds a threshold.

4. The filling device according to claim 1, further comprising a pressure data store configured to store data related to pressure values detected by the pressure detection system, wherein the filling device is further configured so that the increase criterion depends on data stored in the data store.

5. The filling device according to claim 1, further configured so that the increase criterion is fulfilled if the current pressure value assumes or exceeds an extremum.

6. The filling device according to claim 1, further configured so that the increase criterion is fulfilled if the current pressure value either reaches or exceeds a threshold or if the current pressure value assumes or exceeds an extremum, in particular a maximum.

7. A filling controller configured to control the filling process performed by a filling device of claim 1, the filling controller comprising:
a volume control module configured to direct the volume control system to increase or decrease a volume of the administration container,
a pressure detection module configured to detect a pressure value related to the pressure inside the supply container by using the pressure detection system, and
a filling module configured to perform the process steps of filling the administration container by:
directing the volume control module to decrease the volume of the administration container,
directing the pressure detection module to detect a pressure value, and
directing the volume control module to increase the volume of the administration container if an increase criterion depending on the pressure value is fulfilled.

8. The filling controller according to claim 7, wherein the filling module is further configured to repeat the process steps of filling the administration container a fixed number of times and/or until a fill level of the administration container reaches a threshold, wherein the filling controller includes a fill level detection module configured to detect a fill level of the administration container using a fill level detection system.

9. The filling controller according to claim 7, further comprising a pressure data store configured to store data related to pressure values detected by a pressure detection system, wherein the filling module is configured that the increase criterion depends on data stored in the data store.

10. The filling controller according to claim 7, wherein the filling module is further configured so that the increase criterion is fulfilled if the pressure value reaches or exceeds a threshold or an extremum.

11. A method of filling a medical or therapeutic fluid from a supply container containing the medical or therapeutic fluid into an administration container being in fluid connection with the supply container, the method comprising the steps:
decreasing the volume of the administration container,
detecting a pressure value related to a pressure inside the supply container, and
increasing the volume of the administration container if an increase criterion depending on the pressure value is fulfilled.

12. The method according to claim 11, wherein the steps of filling the administration container are repeated, in particular a fixed number of times and/or until a fill level of the administration container reaches a threshold.

13. The method according to claim 11, wherein the increase criterion is fulfilled if the pressure value reaches or exceeds a threshold or an extremum.

14. A computer program product comprising a computer readable medium having stored thereon computer program code configured to be executed on one or more processors of a filling device, of a filling controller, or of an administration device, such that the following steps of filling an administration container are performed: decreasing the volume of the administration container, detecting a pressure value related to a pressure inside the supply container, and increasing the volume of the administration container if an increase criterion depending on the pressure value is fulfilled.

* * * * *